United States Patent [19]

Iwamoto et al.

[11] Patent Number: 5,866,298

[45] Date of Patent: Feb. 2, 1999

[54] RADIATION SENSITIVE COMPOSITION FOR COLOR FILTERS

[75] Inventors: Satoshi Iwamoto, Yokkaichi; Yasumi Wanibe, Nagoya; Hiroaki Nemoto, Yokkaichi; Nobuo Bessho, Yokohama, all of Japan

[73] Assignee: Japan Synthetic Rubber Co., Ltd., Tokyo, Japan

[21] Appl. No.: 754,811

[22] Filed: Nov. 21, 1996

[30] Foreign Application Priority Data

Nov. 22, 1995 [JP] Japan .................................. 7-326246

[51] Int. Cl.$^6$ .............................. G03F 7/031; G02B 5/20
[52] U.S. Cl. ..................... 430/281.1; 430/270.1; 430/916; 430/7
[58] Field of Search .......................... 430/281.1, 7, 916, 430/270.1; 522/9, 16, 39, 63

[56] References Cited

U.S. PATENT DOCUMENTS

| | | |
|---|---|---|
| 3,652,275 | 3/1972 | Baum et al. . |
| 3,784,557 | 1/1974 | Cescon . |
| 4,090,877 | 5/1978 | Streeper . |
| 5,362,603 | 11/1994 | Katoh et al. ............................ 430/7 |

FOREIGN PATENT DOCUMENTS

| | | |
|---|---|---|
| 0 024 629 | 3/1981 | European Pat. Off. . |
| 0 377 182 | 7/1990 | European Pat. Off. . |
| 0 520 364 | 12/1992 | European Pat. Off. . |
| 0 539 606 | 5/1993 | European Pat. Off. . |

*Primary Examiner*—John A. McPherson
*Attorney, Agent, or Firm*—Oblon, Spivak, McClelland, Maier & Neustadt, P.C.

[57] ABSTRACT

A radiation sensitive composition for color filters comprising (A) a colorant, (B) a binder polymer, (C) a polyfunctional monomer, (D) a photopolymerization initiator containing at least one biimidazole compound typified by 2,2'-bis(2-chlorophenyl)-4,4',5,5'-tetrakis(4-ethoxycarbonylphenyl)-biimidazole and 2,2'-bis(2,4-dichlorophenyl)-4,4',5,5'-tetraphenylbiimidazole, and (E) a solvent. The composition can be used for the manufacture of color filters exhibiting excellent photographic sensitivity and superior contrast, while effectively controlling production of residual insoluble material during development process.

11 Claims, No Drawings

RADIATION SENSITIVE COMPOSITION
FOR COLOR FILTERS

BACKGROUND OF THE INVENTION

1. Field of the Invention

The present invention relates to a radiation sensitive composition for color filters used for a color liquid crystal display device or a color image pickup tube element.

2. Description of the Background Art

A color liquid crystal display device is mounted on a portable personal computer. Because of an increased demand for color liquid crystal display devices in recent years, reduction in the cost of color liquid crystal displays has been strongly desired. In particular, color filters which are indispensable parts of the color liquid crystal display device are mainly manufactured by forming patterns utilizing photolithographic etching of a chromium thin film used as a black matrix. The manufacturing cost of this type of color filter is extremely high. In addition, the environmental problem caused by chromium waste fluid materials produced during manufacture of the color filter is a subject of public concern.

As a means for solving these problems, attention has been given in recent years to a method for using a radiation sensitive composition in which a black colorant is dispersed to manufacture the black matrix. In this method, a radiation sensitive composition in which a colorant with a black color, for example, is dispersed is first applied to a substrate, the resulting coated film is irradiated with light through a photomask to cure the exposed part, and the coating is developed using an alkali, for example, as the developing solution, to remove the part of the coating which has not been irradiated, thereby obtaining a specified black color pattern (black matrix). Then, a process comprising the application of a radiation sensitive composition in which a colorant with a red, green, or blue color is dispersed, light irradiation, and the development treatment is carried out for various colors to form pixel arrays of each color on the same substrate. A color filter is obtained in this manner.

However, when a black matrix is manufactured by using a black colorant, a significant amount of the colorant which is a non-photosensitive component must be used to secure a sufficient light shielding effect for the black matrix. A relative decrease in the amount of the photosensitive component and a resulting decrease in the sensitivity of the radiation sensitive composition is unavoidable. Furthermore, because the effective strength of radiation in coated films is reduced due to absorption of light by the colorant or the like, the radiation strength inevitably decreases toward the bottom of the coated film (i.e. the part close to the substrate surface). As a result, the reaction for curing the coated film tends to be insufficient close to the bottom. In some case, the bottom of the pattern may be hollowed out during development of the coating, thereby producing lacks, losses, and under-cuts in part of the formed pattern. In addition, when the effective strength of radiation is decreased, the rate of film retention after development and the strength of the pixels themselves may decrease. As a result, the pixels are easily damaged when a transparent conductive film or a liquid crystal aligning layer are formed over the color filter. Although these problems can be solved to some extent using a high energy radiation, this tends to decrease the production efficiency of the black matrix.

Accordingly, efforts have been made to develop a photopolymerization initiator with a high photo-sensitivity sufficient to provide a reaction for curing the radiation sensitive composition for color filters close to the bottom of the coating. One example is a composition comprising a binder polymer which contains a carboxyl group, a poly-functional acrylate compound such as pentaerythrithol hexacrylate, and a photopolymerization initiator. As the high sensitive photopolymerization initiator used for this type of radiation sensitive composition, 2,2'-bis(2-chlorophenyl)-4,4',5,5'-tetraphenyl biimidazole, 2,2'-bis(2,3-dichlorophenyl)-4,4',5,5'-tetraphenyl biimidazole, and the like, have been proposed (for example, Japanese Patent Applications Laid-open No 75372/1994, No.75373/1994, etc.). The use of 2,2'-bis(2-chlorophenyl)-4,4',5,5'-tetraphenyl biimidazole, 5,5'-tetra(alkoxyphenyl) biimidazole, 5,5'-tetra(dialkoxyphenyl) biimidazole, 2,2'-bis(2-chloro-phenyl)-4,4',2,2'-bis(2-chlorophenyl)-4,4',2,2'-bis(2-chlorophenyl)-4,4',5,5'-tetra(trialkoxyphenyl) biimidazole, and the like as the photopolymerization initiator of the radiation sensitive composition used in a print or photoresist has also been proposed (e.g. Japanese Patent Publication No. 38403/1973 official report, Japanese Patent Application Laid-open No. 174204/1987).

However, these radiation sensitive compositions do not provide a sensitivity of a level sufficient to eliminate the use of the high energy radiation. The above-mentioned problems of lack or loss of patterns, low rate of film retention, and the decreased strength of pixels may still occur if the amount of irradiation is insufficient.

In particular, because the above-mentioned 2,2'-bis(2-chlorophenyl)-4,4',5,5'-tetraphenyl biimidazole is scarcely soluble in solvents, it is impossible to add a large amount of this compound to sufficiently increase the photographic sensitivity. Insoluble or precipitated compounds may cause production of foreign material which may produce projections on pixels which may impair the function of the transparent conductive layer of liquid crystal aligning layer coated on the color filter.

In addition, the radiation sensitive composition using the above-mentioned 2,2'-bis(2-chlorophenyl)-4,4',5,5'-tetraphenyl biimidazole, may leave substances which are insoluble in a developing solution in areas other than the area where the pixels are formed during the development process in the manufacture of color filters. The resulting color filters exhibit low light transmission on the whole. Use of such color filters in a color liquid crystal display device may result in decreased display contrast. In addition, pixels formed by a succeeding process on the part where insoluble material remains exhibit insufficient adhesion to the substrate due to the insoluble material. This may cause peeling of that part from the substrate and production of damaged parts in the color filters.

Development of a new photopolymerization initiator which can solve these various problems has therefore been desired. In spite of the extreme difficulty in anticipating the relationship between the structure of a photopolymerization initiator and its characteristics, development of a photopolymerization initiator which can provide the radiation sensitive composition exhibiting excellent sensitivity and contrast, which produces no insoluble material during the development treatment has been strongly desired.

The present invention has been achieved in view of this situation and has an object of providing a radiation sensitive composition for color filters which can exhibit excellent photographic sensitivity and contrast, but does not produce any insoluble material during the development treatment.

SUMMARY OF THE INVENTION

The above first object can be attained in the present invention by a radiation sensitive composition for color filters comprising:

(A) a colorant, (B) a binder polymer, (C) a poly-functional monomer, (D) a photopolymerization initiator which is at least one biimidazole compound selected from the group consisting of the compounds represented by the following general formula (1),

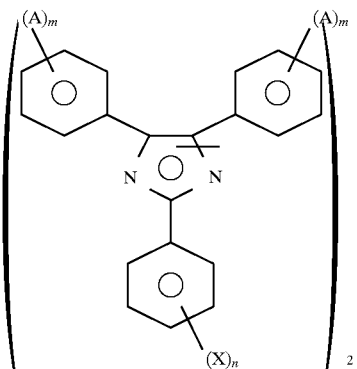

wherein X is a hydrogen atom, a halogen atom, a cyano group, an alkyl group having 1 to 4 carbon atoms, or an aryl group having 6 to 9 carbon atoms, A is a —COO—R group (wherein R is an alkyl group having 1 to 4 carbon atoms or an aryl group having 6 to 9 carbon atoms), m is an integer from 1 to 3, and n is an integer from 1 to 3, or the compounds represented by the following general formula (2),

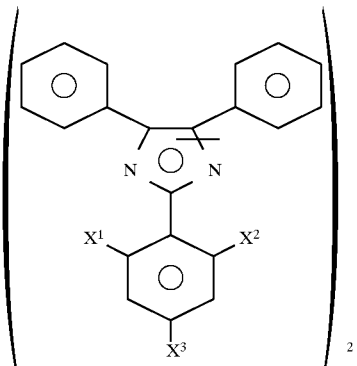

wherein $X^1$, $X^2$, and $X^3$ may be the same or different and each independently represents a hydrogen atom, a halogen atom, a cyano group, an alkyl group having 1 to 4 carbon atoms, or an aryl group having 6 to 9 carbon atoms, provided that two or more of $X^1$, $X^2$, and $X^3$ may not be a hydrogen atom at the same time, and (E) a solvent.

Other objects, features and advantages of the invention will hereinafter become more readily apparent from the following description.

DETAILED DESCRIPTION OF THE INVENTION AND PREFERRED EMBODIMENTS

The present invention will now be explained in detail.

(A) Colorant

The colorant in the present invention is suitably selected to correspond to the use of the color filter. Either an inorganic colorant or an organic colorant may be used with no limitations on the color tone.

The organic colorant may be a dye, an organic pigment, a natural coloring substance, or the like. The inorganic colorant may include inorganic salts called body pigments, in addition to inorganic pigments. Because color filters require a high degree of color display and heat resistance, colorants capable of displaying colors at a high intensity and highly resistive to heat, particularly those highly resistive to thermal decomposition, are preferred in the present invention. Usually, organic colorants, particularly organic pigments, are preferred.

Compounds classified under "Pigment" in the color index (C.I.; published by The Society of Dyers and Colorists Company), specifically those with the following color index (C.I.) numbers are given as examples.

C.I. Pigment Yellow 12, C.I. Pigment Yellow 13, C.I. Pigment Yellow 14, C.I. Pigment Yellow 17, C.I. Pigment Yellow 20, C.I. Pigment Yellow 24, C.I. Pigment Yellow 31, C.I. Pigment Yellow 55, C.I. Pigment Yellow 83, C.I. Pigment Yellow 93, C.I. Pigment Yellow 109, C.I. Pigment Yellow 110, C.I. Pigment Yellow 139, C.I. Pigment Yellow 153, C.I. Pigment Yellow 154, C.I. Pigment Yellow 166, C.I. Pigment Yellow 168; C.I. Pigment Orange 36, C.I. Pigment Orange 43, C.I. Pigment Orange 51; C.I. Pigment Red 9, C.I. Pigment Red 97, C.I. Pigment Red 122, C.I. Pigment Red 123, C.I. Pigment Red 149, C.I. Pigment Red 176, C.I. Pigment Red 177, C.I. Pigment Red 180, C.I. Pigment Red 215; C.I. Pigment Violet 19, Pigment Violet 23, Pigment Violet 29; C.I. Pigment Blue 15, C.I. Pigment Blue 15:3, C.I. Pigment Blue 15:6; C.I. pigment green 7, C.I. pigment green 36; C.I. Pigment Brown 23, C.I. Pigment Brown 25; C.I. Pigment Black 1, and Pigment Black 7.

Given as examples of the inorganic colorant are titanium oxide, barium sulfate, zinc white, lead sulfate, yellow lead, zinc yellow, iron oxide red (red iron oxide (III)), cadmium red, ultramarine blue, iron blue, chromium oxide green, cobalt green, amber, titanium black, synthetic iron black, and carbon black.

These colorants can be used alone or in combination of two or more of them.

The colorant in the present invention can be used together with a dispersing agent if desired. Surfactants such as cationic surfactants, anionic surfactants, nonionic surfactants, amphoteric surfactants, silicon-containing surfactants, and fluorine-containing surfactants can be given as examples of the dispersing agent. Specific examples of the surfactants include polyoxyethylene alkyl ethers such as polyoxyethylene lauryl ether, polyoxyethylene stearyl ether, and polyoxyethylene oleyl ether; polyoxyethylene alkyl phenyl ethers such as polyoxyethylene octylphenyl ether and polyoxyethylene nonyl phenyl ether; polyethylene glycol diesters such as polyethylene glycol dilaurate and polyethylene glycol distearate; sorbitan fatty acid esters; fatty acid denatured polyesters; tertiary amine denatured polyurethanes; and products commercially available under the trademarks of KP (manufactured by Shin-Etsu Chemical Co., Ltd.); Polyflow (manufactured by Kyoeisha Chemical Co., Ltd.); F-Top (manufactured by Tochem Products Co., Ltd.); Megafac (manufactured by Dainippon Ink and Chemicals, Inc.); Fluorade (manufactured by Sumitomo 3M Co., Ltd.); and Asahi Guard, Surflon (manufactured by Asahi Glass Co., Ltd.).

These surfactants can be used alone or in combination of two or more of them.

These surfactants are incorporated usually in an amount of 30 parts by weight or less, preferably 5–20 parts by weight, for 100 parts by weight of the colorant.

(B) Binder Polymer

Any polymer can be used as the binder polymer in the present invention provided that such a polymer can act as a binder for the colorant and is soluble in the developing solution, particularly in an alkali developing solution, used in the development treatment in the manufacture of the color filter. The binder polymer preferably used in the present invention is a copolymer made from a monomer mixture which contains an ethylenically unsaturated monomer having at lease one carboxyl group (hereinafter referred to as "carboxyl group-containing unsaturated monomer") and another copolymerizable ethylenically unsaturated monomer (hereinafter simply referred to as "unsaturated monomer"). This copolymer is hereinafter called "carboxyl group-containing copolymer (b)".

Given as examples of the carboxyl group-containing unsaturated monomer are unsaturated monocarboxylic acids, such as acrylic acid, methacrylic acid, crotonic acid, α-chloroacrylic acid, ethacrylic acid, and cinnamic acid; unsaturated dicarboxylic acids (or anhydrides), such as maleic acid, maleic anhydride, fumaric acid, itaconic acid, itaconic anhydride, citraconic acid, citraconic anhydride, and mesaconic acid; and unsaturated poly(tri or higher) valent carboxylic acids (or anhydrides).

These carboxyl group-containing ethylenically unsaturated monomers can be used alone or in combination of two or more of them.

Examples of the above-described other unsaturated monomers are aromatic vinyl compounds such as styrene, α-methyl styrene, vinyl toluene, chlorostyrene, and methoxystyrene; unsaturated carboxylic acid esters such as methyl acrylate, methyl methacrylate, ethyl acrylate, ethyl methacrylate, propyl acrylate, propyl methacrylate, butyl acrylate, butyl methacrylate, 2-hydroxyethyl acrylate, 2-hydroxyethyl methacrylate, benzyl acrylate, and benzyl methacrylate; unsaturated carboxylic acid amino alkyl esters such as amino ethyl acrylate, amino ethyl methacrylate, amino propyl acrylate, and amino propyl methacrylate; unsaturated carboxylic acid glycidyl esters such as glycidyl acrylate and glycidyl methacrylate; carboxylic acid vinyl esters such as vinyl acetate, vinyl propionate, vinyl butyrate, and vinyl benzoate; unsaturated ethers such as vinyl methyl ether, vinyl ethyl ether, allyl glycidyl ether, methallyl glycidyl ether; cylonitrile, α-chloroacrylonitrile, and cyanated vinylidene; unsaturated amide or unsaturated imides such as acrylamides, methacrylamide, α-chloroacrylamide, N-hydroxyethyl acrylamide, N-hydroxyethyl methacrylamide, and maleimide; aliphatic conjugated dienes such as 1,3-butadiene, isoprene, and chloroprene; and macro monomers having a mono-acryloyl group or a mono-methacryloyl group in the molecule chain terminal of a polymer such as polystyrene, polymethyl acrylate, polymethyl methacrylate, polybutyl acrylate, polybutyl methacrylate, or polysilicone.

These other unsaturated monomers can be used alone or in combination of two or more of them.

A copolymer preferred as the carboxyl group-containing copolymer (b) is that obtained by the copolymerization of ① acrylic acid and/or a methacrylic acid and ② at least one unsaturated monomer selected from the group consisting of methyl methacrylate, 2-hydroxyethyl acrylate, 2-hydroxyethyl methacrylate, benzyl acrylate, benzyl methacrylate, styrene, a polystyrene macro monomer, and a polymethyl methacrylate macro monomer.

Given as specific examples of the carboxyl group-containing copolymer (b) are acrylic acid/benzyl acrylate copolymer, acrylic acid/benzyl acrylate/styrene copolymer, acrylic acid/methyl acrylate/styrene copolymer, acrylic acid/benzyl acrylate/polystyrene macro monomer copolymer, acrylic acid/benzyl acrylate/polymethyl methacrylate macro monomer copolymer, acrylic acid/methyl acrylate/polystyrene macro monomer copolymer, acrylic acid/methyl acrylate/polymethyl methacrylate macro monomer copolymer, acrylic acid/benzyl methacrylate copolymer, acrylic acid/benzyl acrylate/styrene copolymer, acrylic acid/methyl acrylate/styrene copolymer, acrylic acid/benzyl acrylate/polystyrene macro monomer copolymer, acrylic acid/benzyl acrylate/polymethyl methacrylate macro monomer copolymer, acrylic acid/methyl acrylate/polystyrene macro monomer copolymer, acrylic acid/methyl acrylate/polymethyl methacrylate macro monomer copolymer, acrylic acid/benzyl methacrylate copolymer, acid/methyl methacrylate/polymethyl methacrylate macro monomer copolymer, methacrylic acid/2-hydroxyethyl methacrylate/benzyl methacrylate/polystyrene macro monomer copolymer, and methacrylic acid/2-hydroxyethyl methacrylate/benzyl methacrylate/polymethyl methacrylate macro monomer copolymer.

Of these carboxyl group-containing copolymers (b), particularly preferred are methacrylic acid/benzyl methacrylate copolymer, methacrylic acid/benzyl methacrylate/styrene copolymer, methacrylic acid/methyl methacrylate/styrene copolymer, methacrylic acid/benzyl methacrylate/polystyrene macro monomer copolymer, methacrylic acid/benzyl methacrylate/polymethyl methacrylate macro monomer copolymer, methacrylic acid/methyl methacrylate/polystyrene macro monomer copolymer, methacrylic acid/methyl methacrylate/polymethyl methacrylate macro monomer copolymer, methacrylic acid/2-hydroxyethyl methacrylate/benzyl methacrylate/polystyrene macro monomer copolymer, and methacrylic acid/2-hydroxyethyl methacrylate/benzyl methacrylate/polymethyl methacrylate macro monomer copolymer.

The proportion of carboxyl group-containing unsaturated monomers in the carboxyl group-containing copolymer (b) is usually 5–50 wt %, and preferably 10–40 wt %. If this proportion of carboxyl group-containing unsaturated monomers is less than 5 wt %, the solubility of the resulting radiation sensitive composition in an alkaline developing solution tends to be reduced; if more than 50 wt %, the pixels formed tends to drop out from the substrate or the pixel surface tends to be easily damaged during development using an alkaline developing solution.

The carboxyl group-containing copolymer (b) which contains the above-described carboxyl group-containing unsaturated monomers at the above-mentioned specific copolymerization rate particularly exhibits superior solubility in an alkaline developing solution, and thus helps the radiation sensitive composition in which this copolymer is used as a binder to leave almost no undissolvable substance, greasing in the area on the substrate other than the part where pixels are formed, and residual membranes after development using an alkaline developing solution. In addition, the pixels obtained from this composition are not excessively dissolved in an alkaline developing solution, exhibit superior adhesion to the substrate, and are free from the risk of dropping out of the substrate.

The binder polymer has a polystyrene reduced weight average molecular weight measured by gel permeation chromatography (GPC, the eluent is tetrahydrofuran.) (hereinafter simply referred to as "weight average molecular weight") of 3,000–300,000, and preferably of 5,000–100,000.

The use of the binder polymer which has such a specific weight average molecular weight ensures production of a radiation sensitive composition which is excellently developed and makes it possible to form pixel arrays having sharp pattern edges, while minimizing greasing or residual coatings in the area of the substrate other than the part where pixels are formed during the development treatment.

The proportion of binder polymer in the present invention is usually 10–1000 parts by weight, preferably 20–500 parts by weight, for 100 parts by weight of the colorant (A). If the proportion of binder polymer is less than 10 parts by weight, development in an alkaline developing solution may be impaired, resulting in production of greasing or residual coatings during the development in the area on the substrate other than the part where pixels are formed. The proportion of binder polymer exceeding 1,000 parts by weight, on the other hand, results in a relative decrease in the amount of colorant, which may make it difficult to achieve the target color density in the thin film.

(C) Poly-Functional Monomer

The following compound can be given as examples of the poly-functional monomer used in the present invention: diacrylates or dimethacrylates of an alkylene glycol such as ethylene glycol or propylene glycol; diacrylates or dimethacrylates of polyalkylene glycol such as polyethylene glycol or polypropylene glycol; polyacrylates or polymethacrylates of a poly(tri or higher)hydric alcohol such as glycerol, trimethylolpropane, pentaerythritol, or dipentaerythritol; oligo acrylates or oligo methacrylates of polyester, an epoxy resin, a urethane resin, an alkyd resin, a silicone resin, or a spirane resin; di(meth)acrylates of both terminal hydroxylated polymer such as both terminal hydroxy polybutadienes, both terminal hydroxy polyisoprenes, and both terminal hydroxy polycaprolactones; tris acryloyloxy ethyl phosphate, tris methacryloyloxy ethyl phosphate, and the like.

Of these poly-functional monomers, especially preferred are polyacrylates or polymethacrylates of a poly(tri or higher)hydric alcohol, specifically compounds such as trimethylolpropane triacrylate, trimethylolpropane trimethacrylate, pentaerythritol triacylate, pentaerythritol trimethacrylate, pentaerythritol tetracrylate, pentaerythritol tetramethacrylate, dipentaerythritol hexacrylate, and dipentaerythritol hexamethacrylate. In particular, the use of trimethylolpropane triacrylate, pentaerythritol triacylate, or dipentaerythritol hexacrylate is preferred to obtain a high pixel strength, and smooth pixel surfaces, and to minimize greasing or residual coatings in the area on the substrate other than the part where pixels are formed.

The proportion of the poly-functional monomer in the present invention is usually 5–500 parts by weight, and preferably 20–300 parts by weight, for 100 parts by weight of the binder polymer(B). If this proportion of the poly-functional monomer is less than 5 parts by weight, the pixel strength and the surface smoothness of the pixels tend to be insufficient; if more than 500 parts by weight, the resultant coating may be developed only with difficulty by an alkaline developing solution and greasing or residual coatings may be left in the area on the substrate other than the part where pixels are formed.

(D) Photopolymerization Initiator

The photopolymerization initiator in the present invention contains as an essential compound at least one biimidazole compound selected from the group consisting of the compounds represented by the above-described general formula (1) (hereinafter referred to as biimidazole compounds (1)) and the compounds represented by the above-described general formula (2) (hereinafter referred to as biimidazole compounds (2)).

The general formulas (1) and (2) show structures in which two imidazole units are mutually bonded via the 1 position or the 2 position. Accordingly, the biimidazole compound (1) and the biimidazole compound (2) are respectively either one of the compounds of the following formulas (3)–(5) or a mixture of two or more of these compounds.

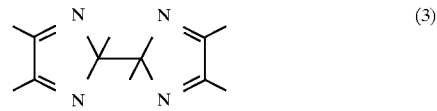

(3)

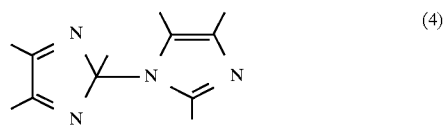

(4)

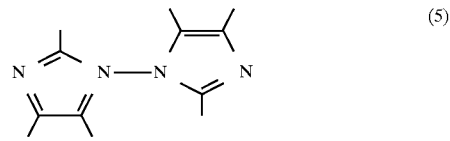

(5)

In the general formula (1), given as examples of the halogen atom X are a chlorine atom, bromine atom, and iodine atom; as examples of the alkyl group having 1–4 carbon atoms are a methyl group, ethyl group, n-propyl group, iso-propyl group, n-butyl group, iso-butyl group, and test-butyl group; as examples of the aryl group of having 6–9 carbon atoms are a phenyl group, ortho-tolyl group, meta-tolyl group, and para-tolyl.

Further, given as examples of R in —COO—R which is shown by the symbol A are the same alkyl group having 1–4 carbon atoms and the same aryl group having 6–9 carbon atoms which were described in connection with the group X.

The following compounds are given as specific examples of the biimidazole compound (1) and biimidazole compound (2). The biimidazole compound (1) include such compounds as:

2,2'-bis(2-chlorophenyl)-4,4',5,5'-tetrakis(4-ethoxycarbonylphenyl)biimidazole,
2,2'-bis(2-chlorophenyl)-4,4',5,5'-tetrakis(4-phenoxycarbonylphenyl)biimidazole,
2,2'-bis(2,4-dichlorophenyl)-4,4',5,5'-tetrakis(4-ethoxycarbonylphenyl)biimidazole,
2,2'-bis(2,4-dichlorophenyl)-4,4',5,5'-tetrakis(4-phenoxycarbonylphenyl)biimidazole,
2,2'-bis(2,4,6-trichlorophenyl)-4,4',5,5'-tetrakis(4-ethoxycarbonylphenyl)biimidazole,
2,2'-bis(2,4,6-trichlorophenyl)-4,4',5,5'-tetrakis(4-phenoxycarbonylphenyl)biimidazole,
2,2'-bis(2-cyanophenyl)-4,4',5.5'-tetrakis(4-ethoxycarbonylphenyl)biimidazole,
2,2'-bis(2-cyanophenyl)-4,4',5,5'-tetrakis(4-phenoxycarbonylphenyl)biimidazole,
2,2'-bis(2-methylphenyl)-4,4',5,5'-tetrakis(4-methoxycarbonylphenyl)biimidazole,
2,2'-bis(2-methylphenyl)-4,4',5,5'-tetrakis(4-ethoxycarbonylphenyl)biimidazole,
2,2'-bis(2-methylphenyl)-4,4',5,5'-tetrakis(4-phenoxycarbonylphenyl)biimidazole,
2,2'-bis(2-ethyl phenyl)-4,4',5,5'-tetrakis(4-methoxycarbonylphenyl)biimidazole,
2,2'-bis(2-ethylphenyl)-4,4',5,5'-tetrakis(4-ethoxycarbonylphenyl)biimidazole,
2,2'-bis(2-ethylphenyl)-4,4',5,5'-tetrakis(4-phenoxycarbonylphenyl)biimidazole, 2,2'-bis(2-phenylphenyl)-4,4',5,5'-tetrakis(4-methoxycarbonylphenyl)biimidazole,
2,2'-bis(2-phenylphenyl)-4,4',5,5'-tetrakis(4-ethoxycarbonylphenyl)biimidazole, and
2,2'-bis(2-phenylphenyl)-4,4',5,5'-tetrakis(4-phenoxycarbonylphenyl)biimidazole.

The biimidazole compound (2) include such compounds as:
2,2'-bis(2,4-dichlorophenyl)-4,4',5,5'-tetraphenyl biimidazole,
2,2'-bis(2,4,6-trichlorophenyl)-4,4',5,5'-tetraphenylbiimidazole,
2,2'-bis(2,4-dibromophenyl)-4,4',5,5'-tetraphenylbiimidazole,
2,2'-bis(2,4,6-tribromophenyl)-4,4',5,5'-tetraphenylbiimidazole,
2,2'-bis (2,4-dicyanophenyl)-4,4',5,5'-tetraphenyl biimidazole,
2,2'-bis (2,4,6-tricyanophenyl)-4,4',5,5'-tetra phenylbiimidazole,
2,2'-bis(2,4-dimethyl phenyl)-4,4',5,5'-tetraphenylbiimidazole,
2,2'-bis(2,4,6-trimethylphenyl)-4,4',5,5'-tetraphenylbiimidazole,
2,2'-bis(2,4-diethyl phenyl)-4,4',5,5'-tetraphenyl biimidazole,
2,2'-bis(2,4,6-triethylphenyl)-4,4',5,5'-tetraphenylbiimidazole,
2,2'-bis(2,4-di phenyl phenyl)-4,4',5,5'-tetraphenylbiimidazole, and
2,2'-bis(2,4,6-triphenylphenyl)-4,4',5,5'-tetraphenylbiimidazole.

Of these, particularly preferred biimidazole compounds (1) are: 2,2'-bis(2-chlorophenyl)-4,4',5,5'-tetrakis(4-ethoxycarbonylphenyl) biimidazole and 2,2'-bis(2-bromophenyl)-4,4',5,5'-tetrakis(4-ethoxycarbonylphenyl) biimidazole, and particularly preferred biimidazole compounds (2) are 2,2'-bis(2,4-dichlorophenyl)-4,4',5,5'-tetraphenyl biimidazole, 2,2'-bis(2,4-dibromophenyl)-4,4',5,5'-tetraphenyl biimidazole, 2,2'-bis(2,4,6-trichlorophenyl)-4,4',5,5'-tetraphenyl biimidazole, and 2,2'-bis(2,4,6-tribromophenyl)-4,4',5,5'-tetraphenyl biimidazole.

The biimidazole compounds (1) and biimidazole compounds (2) are abundantly soluble in solvents, produces almost no foreign material such as insoluble material and precipitates, exhibit high sensitivity to cause the curing reaction to progress sufficiently by irradiation using a small dose of radiation energy. The resulting cured product exhibits a high contrast with no curing reaction occurring in the area where there has been no irradiation, so that the coated film after irradiation is clearly divided into a cured part insoluble in a developing solution and an uncured part easily soluble in the developing solution. An excellent color filter with no lack or loss of pattern and no under-cut can therefore be obtained.

In the present invention, the biimidazole compounds (1) and the biimidazole compounds (2) may be used either individually or in combinations of two or more. Any optional biimidazole compound (1) and biimidazole compound (2) can be used jointly.

The proportion of the biimidazole compounds (1) and (2) used in the present invention is usually 0.01–200 parts by weight, preferably 1–120 parts by weight, and particularly preferably 1–50 parts by weight, for 100 parts by weight of the poly-functional monomer (C). If this proportion is less than 0.01 part by weight, curing of the composition by light irradiation may occur only insufficiently, resulting in inadequacy, loss or under-cut in the patterns produced. If the proportion of the biimidazole compounds (1) and (2) is more than 200 parts by weight, on the other hand, the patterns formed tend to be easily dropped out of the substrate during development, and greasing or residual membrane may be produced in the area where no patterns are formed.

In addition to the biimidazole compounds (1) and/or the biimidazole compounds (2), one or more other additives, such as a photo-radical generator other than the biimidazole compounds (1) or (2) (hereinafter called "other photo-radical generator"), a sensitizing agent, a curing promoter, and a photo-cross-linking agent or photosensitizer consisting of one or more high molecular weight compounds (hereinafter referred to as "high polymer photo-cross-linking agent or photosensitizer"), may be used in the present invention as the photopolymerization initiator of component (D).

Given as the examples of the other photo-radical generator are tris(2,4,6-trichloromethyl)-s-triazine, 2-phenylbis(4,6-trichloromethyl)-s-triazine, 2-(4-chlorophenyl)-bis(4,6-trichloromethyl)-s-triazine, 2-(3-chlorophenyl)-bis(4,6-trichloromethyl)-s-triazine, 2-(2-chlorophenyl)-bis(4,6-trichloromethyl)-s-triazine, 2-(4-methoxyphenyl)-bis(4,6-trichloromethyl)-s-triazine, 2-(3-methoxyphenyl)-bis(4,6-trichloromethyl)-s-triazine, 2-(2-methoxyphenyl)-bis(4,6-trichloromethyl)-s-triazine, 2(4-methylthiophenyl)-bis(4,6-trichloromethyl)-s-triazine, 2-(3-methylthiophenyl)-bis(4,6-trichloromethyl)-s-triazine, 2-(2-methylthiophenyl)-bis(4,6-trichloromethyl)-s-triazine, 2-(4-methoxynaphthyl)-bis(4,6-trichloromethyl)-s-triazine, 2-(3-methoxynaphthyl)-bis(4,6-trichloromethyl)-s-triazine, 2-(2-methoxynaphthyl)-bis(4,6-trichloromethyl)-s-triazine, 2-(4-methoxy-β-styryl)-bis(4,6-trichloromethyl)-s-triazine, 2-(3-methoxy-β-styryl)-bis(4,6-trichloromethyl)-s-triazine, 2-(2-methoxy-β-styryl)-bis(4,6-trichloromethyl)-s-triazine, 2-(3,4,5-trimethoxy-β-styryl)-bis(4,6-trichloromethyl)-s-triazine, 2-(4-methylthio-β-styryl)-bis(4,6-trichloromethyl)-s-triazine, 2-(3-methylthio-β-styryl)-bis(4,6-trichloromethyl)-s-triazine, 2-(2-methylthio-β-styryl)-bis(4,6-trichloromethyl)-s-triazine, 2-[(2'-furyl)ethylidene]-4,6-bis(tribromomethyl)-s-triazine, 2-[(3'-furyl)ethylidene]-4,6-bis(tribromomethyl)-s-triazine, 2-[(3'-methyl-2'-furyl)ethylidene]-4,6-bis(tribromomethyl)-s-triazine, 2-[(4'-methyl-2'-furyl)ethylidene]-4,6-bis(tribromomethyl)-s-triazine, 2-[(5'-methyl-2'-furyl)ethylidene]-4,6-bis(tribromomethyl)-s-triazine, 2-[(2'-methyl-3'-furyl)ethylidene]-4,6-bis(tribromomethyl)-s-triazine, 2-[(4'-methyl-3'-furyl)ethylidene]-4,6-bis(tribromomethyl)-s-triazine, 2-[(5'-methyl-3'-furyl)ethylidene]-4,6-bis(tribromomethyl)-s-triazine, 2-[(4'-ethyl-2'-furyl)ethylidene]-4,6-bis(tribromomethyl)-s-triazine, 2-[(5'-ethyl-2'-furyl)ethylidene]-4,6-bis(tribromomethyl)-s-triazine, 2-[(4'-ethyl-3'-furyl)ethylidene]-4,6-bis(tribromomethyl)-s-triazine, 2-[(5'-ethyl-3'-furyl)ethylidene]-4,6-bis(tribromomethyl)-s-triazine, 2-[(4'-t-butyl-2'-furyl)ethylidene]-4,6-bis(tribromomethyl)-s-triazine, 2-[(5'-t-butyl-2'-furyl)ethylidene]-4,6-bis(tribromomethyl)-s-triazine, 2-[(2'-furyl)ethylidene]-4,6-bis(trichloromethyl)-s-triazine, 2-[(3'-furyl)ethylidene]-4,6-bis(trichloromethyl)-s-triazine, 2-[(3'-methyl-2'-furyl)ethylidene]-4,6-bis(trichloromethyl)-s-triazine, 2-[(4'-methyl-2'-furyl)ethylidene]-4,6-bis(trichloromethyl)-s-triazine, 2-[(5'-methyl-2'-furyl)ethylidene]-4,6-bis(trichloromethyl)-s-triazine, 2-[(2'-methyl-3'-furyl)ethylidene]-4,6-bis(trichloromethyl)-s-triazine, 2-[(4'-methyl-3'-furyl)ethylidene]-4,6-bis(trichloromethyl)-s-triazine, 2-[(5'-methyl-3'-furyl)ethylidene]-4,6-bis(trichloromethyl)-s-triazine, 2-[(4'-ethyl-2'-furyl)

ethylidene]-4,6-bis(trichloromethyl)-s-triazine, 2-[(5'-ethyl-2'-furyl)ethylidene]-4,6-bis(trichloromethyl)-s-triazine, 2-[(4'-ethyl-3'-furyl)ethylidene]-4,6-bis(trichloromethyl)-s-triazine, 2-[(5'-ethyl-3'-furyl)ethylidene]-4,6-bis(trichloromethyl)-s-triazine, 2-[(5'-propyl-2'-furyl)ethylidene]-4,6-bis(trichloromethyl)-s-triazine, 2-[(4'-t-butyl-2'-furyl)ethylidene]-4,6-bis(trichloromethyl)-s-triazine, 2-[(5'-t-butyl-2'-furyl)ethylidene]-4,6-bis(trichloromethyl)-s-triazine, 2-[(4'-t-butyl-3'-furyl)ethylidene]-4,6-bis(trichloromethyl)-s-triazine, 2-[(5'-t-butyl-3'-furyl)ethylidene]-4,6-bis(trichloromethyl)-s-triazine, 2-[(3',4'-dimethyl-2'-furyl)ethylidene]-4,6-bis(trichloromethyl)-s-triazine, 2-[(4',5'-dimethyl-2'-furyl)ethylidene]-4,6-bis(trichloromethyl)-s-triazine, 2-[(3',4'-dit-butyl-2'-furyl)ethylidene]-4,6-bis(trichloromethyl)-s-triazine, 2-[(4',5'-dit-butyl-2'-furyl)ethylidene]-4,6-bis(trichloromethyl)-s-triazine, 2-[(3',4',5'-trimethyl-2'-furyl)ethylidene]-4,6-bis(trichloromethyl)-s-triazine, 2-[(5'-chloro-2'-furyl)ethylidene]-4,6-bis(trichloromethyl)-s-triazine, 2-[(4'-hydroxy-2'-furyl)ethylidene]-4,6-bis(trichloromethyl)-s-triazine, 2-[(5'-hydroxy-2'-furyl)ethylidene]-4,6-bis(trichloromethyl)-s-triazine, 2-[(5'-cyano-2'-furyl)ethylidene]-4,6-bis(trichloromethyl)-s-triazine, 2-[(5'-nitro-2'-furyl)ethylidene]-4,6-bis(trichloromethyl)-s-triazine, 2-[(4'-carboxy-2'-furyl)ethylidene]-4,6-bis(trichloromethyl)-s-triazine, 2-[(4'-phenyl-2'-furyl)ethylidene]-4,6-bis(trichloromethyl)-s-triazine, 2-[(5'-phenyl-2'-furyl)ethylidene]-4,6-bis(trichloromethyl)-s-triazine, 2-[(5'-thioethyl-2'-furyl)ethylidene]-4,6-bis(trichloromethyl)-s-triazine, 2-[(4'-thiophenyl-2'-furyl)ethylidene]-4,6-bis(trichloromethyl)-s-triazine, 2-[(4'-methoxy-2'-furyl)ethylidene]-4,6-bis(trichloromethyl)-s-triazine, 2-[(5'-ethoxy-2'-furyl)ethylidene]-4,6-bis(trichloromethyl)-s-triazine, 2-[(4'-dimethylamino-2'-furyl)ethylidene]-4,6-bis(trichloromethyl)-s-triazine, 2-[(5'-diethylamino-2'-furyl)ethylidene]-4,6-bis(trichloromethyl)-s-triazine, 2-[(5'-acetyl-2'-furyl)ethylidene]-4,6-bis(trichloromethyl)-s-triazine, 2-[(5'-benzyl-2'-furyl)ethylidene]-4,6-bis(trichloromethyl)-s-triazine, 2-hydroxy-2-methyl-1-phenylpropan-1-one, 1-(4-isopropylphenyl)-2-hydroxy-2-methylpropan-1-one, 4-(2-hydroxyethoxy)phenyl-(2-hydroxy-2-propyl) ketone, 1-hydroxycyclohexylphenyl ketone, 2,2-dimethoxy-2-phenylacetophenone, 2-methyl-(4-methylthiophenyl)-2-morpholino-1-propan-1-one, 2-benzyl-2-dimethylamino-1-(4-morpholinophenyl)butan-1-one, benzophenone, 4,4'-bis(dimethylamino) benzophenone, 4,4'-bis(diethylamino) benzophenone, 2,4-diethylthioxanthone, 3,3-dimethyl-4-methoxybenzophenone, 4-azidobenzaldehyde, 4-azidoacetophenone, 4-azidobenzalacetophenone, azidopyrene, 4-diazodiphenylamine, 4-diazo-4'-methoxydiphenylamine, 4-diazo-3-methoxydiphenylamine, bis(2,6-dimethoxybenzoyl)-2,4,4-trimethylpentylphosphine oxides, dibenzoyl, benzoin isobutyl ether, N-phenylthioacrydone, and triphenylpyrrilium perchlorate. These other photo-radical generators can be used alone or in combination of two or more of them.

Given as examples of the sensitizor are 4-diethylaminoacetophenone, 4-dimethylaminopropylphenone, ethyl-4-dimethylamino benzoate, 2-ethylhexyl-1,4-dimethylamino benzoate, 2,5-bis(4'-diethylaminobenzal)cyclohexanone, 7-diethylamino-3-(4-diethylaminobenzoyl)cumarin, and 4-(diethylamino)chalcone. These sensitizing agents can be used alone or in combination of two or more of them.

Chain transfer agents such as 2-mercaptobenzoimidazole, 2-mercapto-benzothiazole, 2-mercaptobenzoxiazole, 2,5-dimercapto-1,3,4-thiadiazole, and 2-mercapto-4,6-dimethylamino pyridine are given as examples of the curing promoter.

These curing promoters can be used alone or in combination of two or more of them.

Among these other photo-radical generators, sensitizers, and curing promoters, 2-hydroxy-2-methyl-1-phenylpropan-1-one, 2-methyl-(4-methylthiophenyl)-2-morpholino-1-propan-1-one, 2-benzyl-2-dimethylamino-1-(4-morpholinophenyl) butan-1-one, 4,4'-bis(dimethylamino)benzophenone, 4,4'-bis(diethylamino) benzophenone, and 2-mercaptobenzothiazole are preferred in view of preventing the formed pixels from dropping out of the substrate during development and ensuring formation of strong and highly sensitive pixels.

In the present invention, particularly preferred combinations for the photopolymerization initiator (D) are the combinations of a biimidazole compound (1) and/or a biimidazole compound (2), a benzophenone-type photo-radical generator, and a thiazole-type curing promoter.

Specific examples of particularly preferred combinations are 2,2'-bis(2-chlorophenyl)-4,4',5,5'-tetrakis(4-ethoxycarbonylphenyl)biimidazole/4,4'-bis(diethylamino) benzophenone, 2,2'-bis(2-chlorophenyl)-4,4',5,5'-tetrakis(4-ethoxycarbonylphenyl)biimidazole/4,4'-bis(diethylamino) benzophenone/2-benzyl-2-dimethylamino-1-(morpholinophenyl)butan-1-one, 2,2'-bis(2-chlorophenyl)-4,4',5,5'-tetrakis(4-ethoxycarbonylphenyl)biimidazole/4,4'-bis(diethylamino) benzophenone/1-hydroxycyclohexylphenyl ketone, 2,2'-bis(2-chlorophenyl)-4,4',5,5'-tetrakis(4-ethoxycarbonylphenyl)biimidazole/4,4'-bis(dimethylamino)enzophenone/1-hydroxycyclohexylphenyl ketone/2-mercaptoenzothiazole, 2,2'-bis(2,4-dichlorophenyl)-4,4',5,5'-tetraphenylbiimidazole/4,4'-bis(diethylamino) benzophenone, 2,2'-bis(2,4-dibromophenyl)-4,4',5,5'-tetraphenylbiimidazole/4,4'-bis(diethylamino) benzophenone/2-benzyl-2-dimethylamino-1-(4-morpholinophenyl)butan-1-one, 2,2'-bis-(2,4-dibromophenyl)-4,4',5,5'-tetraphenylbiimidazole/4,4'-bis (diethylamino)benzophenone/1-hydroxycyclohexylphenyl ketone, and 2,2'-bis(2,4,6-trichlorophenyl)-4,4',5,5'-tetraphenylbiimidazole/4,4'-bis(dimethylamino) benzophenone/1-hydroxycyclohexylphenyl ketone/2-mercaptobenzothiazole.

The proportion of the other photo-radical generators used in the present invention is preferably 80 wt % or less of the total amount of the photopolymerization initiator (D). The proportion of the photosensitizer and/or the curing promoter used in the present invention is preferably 80 wt % or less of the total amount of the photopolymerization initiator (D).

The above-mentioned high polymer photo-cross-linking-photosensitizer is a high molecular weight compound which possesses a functional group in a main chain and/or a side chain, which functions as a photosensitizer or a photo-cross-linking agent. Typical examples of the high polymer photo-cross-linking-photosensitizer are a condensate of 4-azidobenzaldehyde and polyvinyl alcohol, a condensate of 4-azidobenzaldehyde and a phenol novolak resin, a homopolymer or copolymer of 4-acryloylphenyl cinnamoyl ester, 1,4 -polybutadiene, and 1,2-polybutadiene.

These high polymer photo-cross-linking-photosensitizers can be used alone or in combination of two or more of them.

The proportion of the high polymer photo-cross-linking-photosensitizers used in the present invention is usually 200 parts by weight or less, preferably 0.01–200 parts by weight, and more preferably 50–180 parts by weight, for 100 parts by weight of the biimidazole compounds (1) and (2).

(E) Solvent

Any solvent may be suitably selected for use in the present invention, provided that such solvent can dissolve or disperse the above-mentioned components (A), (B), (C), and (D) and the other additives which may be optionally incorporated, do not react with these components or additives, and exhibit moderate volatility.

Given as examples of such solvents are glycol ethers such as ethylene glycol monomethyl ether and ethylene glycol monoethyl ether; ethylene glycol monoalkyl ether acetates such as ethylene glycol monomethyl ether acetate and ethylene glycol monoethyl ether acetate; diethylene glycol monoalkyl ether such as diethylene glycol monomethyl ether, diethylene glycol monoethyl ether, diethylene glycol monopropyl ether, and diethylene glycol monobutyl ether; propylene glycol monoalkyl ether acetates such as propylene glycol monomethyl ether acetate, propylene glycol monoethyl ether acetate; other ethers such as diethylene glycol dimethyl ether, diethylene glycol diethyl ether, and tetrahydrofuran; ketones, such as methyl ethyl ketone, cyclohexanone, 2-heptanone, and 3-heptanone; lactic acid alkyl esters such as methyl 2-hydroxy propionate, ethyl 2-hydroxy propionate, ethyl 2-hydroxy-2-methyl propionate, methyl 3-methoxy propionate, ethyl 3-methoxy propionate, methyl 3-ethoxy propionate, ethyl 3-ethoxy propionate, ethoxyethyl acetate, hydroxyethyl acetate, methyl 2-hydroxy-3-methyl butanoate, 3-methyl-3-methoxybutyl acetate, and 3-methyl-3-methoxybutyl propionate; other esters such as ethyl acetate, butyl acetate, amyl formate, isoamyl acetate, isobutyl acetate, butyl propionate, isopropyl butyrate, ethyl butyrate, butyl butyrate, methyl pyruvate, ethyl pyruvate, propyl pyruvate, methyl acetoacetate, ethyl acetoacetate, and ethyl 2-oxobutanoate; and aromatic hydrocarbons such as toluene and xylene.

These solvents can be used alone or in combination of two or more of them.

A high-boiling point solvent such as benzyl ethyl ether, dihexyl ether, acetonyl acetone, isophorone, caproic acid, caprylic acid, 1-octanol, 1-nonanol, benzyl alcohol, benzyl acetate, ethyl benzoate, diethyl oxalate, diethyl maleate, γ-butyrolactone, ethylene carbonate, propylene carbonate, or phenyl cellosorb acetate, can be used together with the above-described solvent. These high-boiling point solvents may be used either individually or in combinations of two or more.

Of the above solvents, ethylene glycol monomethyl ether acetate, propylene glycol monomethyl ether acetate, propylene glycol monoethyl ether acetate, diethylene glycol dimethyl ether, cyclohexanone, 2-heptanone, 3-heptanone, ethyl 2-hydroxy propionate, 3-methyl-3-methoxybutyl propionate, ethyl 3-methoxy propionate, methyl 3-ethoxy propionate, ethyl 3-ethoxypropionate, butyl acetate, amyl formate, isoamyl acetate, isobutyl acetate, butyl propionate, isopropyl butyrate, ethyl butyrate, butyl butyrate, and ethyl pyruvate are preferred from the viewpoint of solubility, pigment dispersibility, coatability, and the like. γ-Butyrolactone is preferred among the high-boiling point solvents.

The proportion of the solvent used in the present invention is usually 100–10,000 parts by weight, and preferably 500–5,000 parts by weight, for 100 parts by weight of the binder polymer (B).

(F) Organic Acid

An organic acid may be added to the radiation sensitive composition of the present invention. The addition of the organic acid is useful for improving the solubility of the coating formed by the composition in an alkaline developing solution and for reducing residual insoluble matters after the development treatment, when the binder polymer (B) is a carboxyl group-containing polymer, and particularly when the polymer is the carboxyl group-containing copolymer (b).

An aliphatic carboxylic acid containing a carboxylic acid group or a phenyl group with a molecular weight of 1,000 or less is preferred.

Given as examples of such an aliphatic carboxylic acid are monocarboxylic acids such as formic acid, acetic acid, propionic acid, butyric acid, valeric acid, pivalic acid, caproic acid, diethyl acetic acid, enanthic acid, and caprylic acid; dicarboxylic acids such as oxalic acid, malonic acid, succinic acid, glutaric acid, adipic acid, pimelic acid, suberic acid, azelaic acid, sebacic acid, brassylic acid, methylmalonic acid, ethylmalonic acid, dimethylmalonic acid, methylsuccinic acid, tetra-methylsuccinic acid, cyclohexane dicarboxylic acid, itaconic acid, citraconic acid, maleic acid, fumaric acid, and mesaconic acid; and tricarboxylic acids such as tricarballylic acid, aconitic acid, and camphoronic acid.

Further, given as examples of the phenyl group-containing carboxylic acids are aromatic carboxylic acids with a carboxyl group directly bonded to a phenyl group and carboxylic acids with a carboxyl group bonded to a phenyl group via a carbon chain. Specific examples of these phenyl group-containing carboxylic acids include aromatic monocarboxylic acid such as benzoic acid, toluic acid, cuminic acid, hemellitic acid, and mesitylene acid; aromatic polycarboxylic acids such as phthalic acid, isophthalic acid, terephthalic acid, trimellitic acid, trimesic acid, mellophanic acid, and pyromellitic acid; phenylacetic acid, hydratropic acid, hydrocinnamic acid, mandelic acid, phenylsuccinic acid, atropic acid, cinnamic acid, cinnmylidenic acid, coumaric acid, and umbellic acid.

Of these organic acids, aliphatic dicarboxylic acids and aromatic dicarboxylic acids, such as malonic acid, adipic acid, itaconic acid, citraconic acid, fumaric acid, mesaconic acid, and phthalic acid, are preferred for improving the solubility in an alkaline developing solution or in the solvent (E) or for preventing greasing in the area other than the part in which pixels have been formed.

These organic acids can be used alone or in combination of two or more of them.

The proportion of the organic acid used in the composition of the present invention is usually less than 10 wt %, preferably 0.001–10 wt %, and more preferably 0.01–1 wt %. If this proportion of the organic acid is more than 10 wt %, adhesion of the formed pixels to the substrate tends to be decreased.

Various additives other than the above-described components may be added to the radiation sensitive composition of the present invention as required. Examples of such additives include fillers such as glass and alumina; polymeric compounds such as polyvinyl alcohol, polyethylene glycol monoalkyl ether, and polyfluoroalkyl acrylate; surfactants such as nonionic surfactants, cationic surfactants, and anionic surfactants; adherence promotion agent such as vinyltrimethoxysilane, vinyltriethoxysilane, vinyltris(2-methoxyethoxy)silane, N-(2-aminoethyl)-3-aminopropylmethyldimethoxysilane, N-(2-aminoethyl)-3-aminopropyltrimethoxysilane, 3-aminopropyltriethoxysilane, 3-glycydoxypropyltrimethoxysilane, 3-glycydoxypropylmethyldimethoxysilane, 2-(3,4-epoxycyclohexyl)ethyltrimethoxysilane, 3-chloropropylmethyldimethoxysilane, 3-chloropropyltrimethoxysilane, 3-methacryloxypropyltrimethoxysilane, 3-mercaptopropyltrimethoxysilane; antioxidants such as 2,2-thiobis(4-methyl-6-t-butylphenol) and 2,6-di-t-butylphenol; UV absorbers such as 2-(3-t-butyl-5-methyl-2-hydroxyphenyl)-5-chlorobenzotriaole and alkoxybenzophenone; and flocculation preventives such as sodium polyacrylate.

<Preparation of Color Filters>

The method for preparing color filters using the radiation sensitive composition of the present invention will now be described.

First, a light shielding layer black matrix to define the part in which pixel patterns are produced is formed on the surface of a transparent substrate. A radiation sensitive composition in which a red pigment, for example, is dispersed is applied to this substrate, the composition is prebaked, and the solvent is evaporated, thereby obtaining a coated film. Next, radiation directed onto this coated film through a photomask, following which a development treatment is carried out to dissolve and remove the part of the coated film upon which no light has been shone. A pixel array in which red pixels are arranged in a fixed pattern is thus formed.

Then, application of the composition, prebaking, light irradiation, and the development treatment are carried out for each radiation sensitive composition in which a green or a blue pigment is dispersed, to successively form a green pixel array and a blue pixel array on the same substrate. A color filter with pixel arrays of the three primary colors (red, green, and blue) arranged on the substrate is obtained in this manner.

Glass, silicon, polycarbonate, polyester, aromatic polyamide, polyamideimide, polyimide, and the like can be given as examples of the material for the transparent substrate used in preparing the color filter. The transparent substrate may be previously treated by chemicals such as a silane coupling agent, or by means of a plasma treatment, an ion plating treatment, a sputtering treatment, a vapor phase reaction, or a vacuum deposition.

Revolution, rolling, casting, or any other suitable means can be used to apply the radiation sensitive composition to the transparent substrate. The coating thickness, in terms of the film thickness after drying, is usually 0.1–10 $\mu$m, and preferably 0.2–1.5 $\mu$m.

Visible rays, ultraviolet rays, far ultraviolet rays, electron beams, X-rays, and the like can be used as the source of radiation to form the color filter. Radiation with a wavelength in the range of 190–450 nm is preferred. A preferred dose of radiation energy is in the range of 1–1000 mJ/cm$^2$.

An aqueous solution of a compound such as, for example, sodium carbonate, sodium hydroxide, potassium hydroxide, tetramethylammonium hydroxixde, choline, 1,8-diazabicyclo-[5.4.0]-7-undecene, or 1,5-diazabicyclo-[4.3.0]-5-nonen, can be preferably used as the alkaline developing solution. A suitable amount of a water soluble organic solvent, such as methanol or ethanol, or a surfactant may be added to the alkaline developing solution. Washing is usually carried out after alkali development.

Shower development, spray development, dipping development, paddle development, or the like can be applied as the method for the development treatment under the conditions of room temperature and a length of development of 5–300 seconds.

The color filter thus prepared is very useful as a color liquid crystal display device, a color image pickup tube element, a color sensor, and the like.

Other features of the invention will become apparent in the course of the following description of exemplary embodiments which are given for illustration of the invention and are not intended to be limiting thereof.

EXAMPLES

Comparative Example 1

A radiation sensitive composition was prepared by blending 120 parts by weight of a red pigment (C.I. Pigment Red 177) as the component (A), 50 parts by weight of a copolymer of methacrylic acid/benzyl methacrylate/polystyrene macro monomer (copolymerization weight ratio: 25/65/109; the weight average molecular weight: 55,000) as the component (B), 40 parts by weight of dipentaerythritol pentacrylate as the component (C), 10 parts by weight of 2,2'-bis(2-chlorophenyl)-4,4',5,5'-tetraphenylbiimidazole and 10 parts by weight of 4,4'-bis(diethylamino) benzophenone, as the component (D), and 800 parts by weight of ethylene glycol mono ethyl ether acetate as the component (E).

On the surface of a transparent substrate made of soda glass with a silica (SiO$_2$) membrane produced for preventing elution of sodium ion, this radiation sensitive composition was applied using a spin coater and prebaked for 2 minutes at 80° C., thereby obtaining a coated film with a thickness 1.5 $\mu$m.

Next, after cooling the substrate, the coated film was irradiated with ultraviolet light, containing light of a wavelength of 365 nm, 405 nm and 436 nm, at a dose of 100 mJ/cm$^2$ using a high pressure mercury lamp, for 1 second through a photomask. The substrate was then dipped into a 0.1 wt % tetramethylammonium hydroxide aqueous solution at 25° C. for one minute to develop the coating, washed with pure water, air-dried, and postbaked for 30 minutes at 180° C., to produce a pixel array in which a pattern of red pixels, having a size of 20 $\mu$m×20 $\mu$m each.

The resulting pixel array displyed partial lack of pattern and damage. Under-cut was seen when a section of the pattern was observed using a scanning electron microscope. The observation of the pixel array using an optical microscope revealed the presence of insoluble material on the area where no pattern was formed.

Example 1

A radiation sensitive composition was prepared by blending 120 parts by weight of a red pigment (C.I. Pigment Red 177) as the component (A), 50 parts by weight of a copolymer of methacrylic acid/benzyl methacrylate/polystyrene macro monomer (copolymerization weight ratio: 25/65/10, weight average molecular weight: 55,000) as the component (B), 40 parts by weight of dipentaerythritol pentacrylate as the component (C), 10 parts by weight of 2,2'-bis(2-chlorophenyl)-4,4',5,5'-tetrakis(4-ethoxycarbonylphenyl) biimidazole and 10 parts by weight of 4,4'-bis(diethylamino) benzophenone as the component (D), and 800 parts by weight of ethylene glycol monoethyl ether acetate as the component (E).

A pixel array in which a pattern of red pixels is formed on a substrate was produced in the same manner as in the Comparative Example 1 using this radiation sensitive composition. There was no partial lack of pattern and damage in the resulting pixel array. Observation of a section of the pattern using a scanning electron microscope confirmed no under-cut. Further, the observation of the pixel array using an optical microscope confirmed that there was no insoluble material on the area where no pattern was formed.

Example 2

A radiation sensitive composition was prepared by blending 120 parts by weight of carbon black as the component (A), 50 parts by weight of a copolymer of methacrylic acid/benzyl methacrylate/polystyrene macro monomer (copolymerization weight ratio: 25/65/10, weight average molecular weight: 55,000) as the component (B), 40 parts by weight of dipentaerythritol pentacrylate as the component (C), 10 parts by weight of 2,2'-bis(2-chlorophenyl)-4,4',5, 5'-tetrakis(4-ethoxycarbonylphenyl)biimidazole, 10 parts by weight of 4,4'-bis(diethylamino)benzophenone, and 20 parts by weight of 2-benzyl-2-dimethylamino-1-(4-morpholinophenyl)butan-1-one as the component (D), and 800 parts by weight of ethylene glycol monoethyl ether acetate as the component (E).

A black matrix in which a black pattern is formed on a substrate was produced in the same manner as in the Comparative Example 1 except for using a radiation at a dose of 200 mJ/cm² and using this radiation sensitive composition. There was no partial lack of pattern and damage in the resulting black matrix. Observation of a section of the black matrix using a scanning electron microscope confirmed no under-cut. Further, the observation of the black matrix using an optical microscope confirmed that there was no insoluble material on the area where no pattern was formed.

Example 3

A radiation sensitive composition was prepared by blending 120 parts by weight of a mixture of a red pigment (C.I. Pigment Red 177), an yellow pigment (C.I. Pigment Yellow 83), a green pigment (C.I. Pigment Green 7), and a blue pigment (C.I. Pigment Blue 15:6), at a weight ratio of 10/2/2/5), as the component (A), 50 parts by weight of a copolymer of methacrylic acid/benzyl methacrylate/polystyrene macro monomer (copolymerization weight ratio: 25/65/10, weight average molecular weight: 55,000) as the component (B), 40 parts by weight of dipentaerythritol pentacrylate as the component (C), 10 parts by weight of 2,2'-bis(2-chlorophenyl)-4,4',5,5'-tetrakis(4-ethoxycarbonylphenyl)biimidazole, 10 parts by weight of 4,4'-bis(diethylamino)benzophenone, and 20 parts by weight of 1-hydroxycyclohexylphenyl ketone, as the component (D), and 800 parts by weight of ethylene glycol monoethyl ether acetate as the component (E).

A black matrix in which a black pattern is formed on a substrate was produced in the same manner as in the Example 2 except using this radiation sensitive composition. There was no partial lack of pattern and damage in the resulting black matrix. Observation of a section of the pattern using a scanning electron microscope confirmed no under-cut. Further, the observation of the black matrix using an optical microscope confirmed that there was no insoluble material on the area where no pattern was formed.

Example 4

A radiation sensitive composition was prepared by blending 120 parts by weight of carbon black as the component (A), 50 parts by weight of a copolymer of methacrylic acid/benzyl methacrylate/polystyrene macro monomer (copolymerization weight ratio: 25/65/10, weight average molecular weight: 55,000) as the component (B), 40 parts by weight of dipentaerythritol pentacrylate as the component (C), 10 parts by weight of 2,2'-bis(2-chlorophenyl)-4,4',5, 5'-tetrakis(4-ethoxycarbonylphenyl)biimidazole, 5 parts by weight of 4,4'-bis(dimethylamino)benzophenone, 20 parts by weight of 1-hydroxycyclohexylphenyl ketone, and 2 parts by weight of 2-mercaptobenzothiazole as the component (D), and 800 parts by weight of ethylene glycol monoethyl ether acetate as the component (E).

A black matrix in which a black pattern is formed on a substrate was produced in the same manner as in the Example 2 using this radiation sensitive composition. There was no partial lack of pattern and damage in the resulting black matrix. Observation of a section of the pattern using a scanning electron microscope confirmed no under-cut. Further, the observation of the black matrix using an optical microscope confirmed that there was no insoluble material on the area where no pattern was formed.

Example 5

A radiation sensitive composition was prepared by blending 120 parts by weight of red pigment (C.I. Pigment Red 177) as the component (A), 50 parts by weight of a copolymer of methacrylic acid/benzyl methacrylate/polystyrene macro monomer (copolymerization weight ratio: 25/65/10, weight average molecular weight: 55,000) as the component (B), 40 parts by weight of dipentaerythritol pentacrylate as the component (C), 10 parts by weight of 2,2'-bis(2-dichlorophenyl)-4,4',5,5'-tetrphenylbiimidazole and 10 parts by weight of 4,4'-bis(diethylamino)benzophenone as the component (D), and 800 parts by weight of ethylene glycol monoethyl ether acetate as the component (E).

A pixel array in which a pattern of red pixels is formed on a substrate was produced in the same manner as in the Comparative Example 1 using this radiation sensitive composition. There was no partial lack of pattern and damage in the resulting pixel array. Observation of a section of the pattern using a scanning electron microscope confirmed no under-cut. Further, the observation of the pixel array using an optical microscope confirmed that there was no insoluble material on the area where no pattern was formed.

Example 6

A radiation sensitive composition was prepared by blending 120 parts by weight of carbon black as the component (A), 50 parts by weight of a copolymer of methacrylic acid/benzyl methacrylate/polystyrene macro monomer (copolymerization weight ratio: 25/65/10, weight average molecular weight: 55,000) as the component (B), 40 parts by weight of dipentaerythritol pentacrylate as the component (C), 10 parts by weight of 2,2'-bis(2-dibromophenyl)-4,4', 5,5'-tetrphenylbiimidazole, 10 parts by weight of 4,4'-bis(diethylamino)benzophenone, and 20 parts by weight of 2-benzyl-2-dimethylamino-1-(4-morpholinophenyl)butan-1-one as the component (D), and 800 parts by weight of ethylene glycol monoethyl ether acetate as the component (E).

A black matrix in which a black pattern is formed on a substrate was produced in the same manner as in the Example 2 using this radiation sensitive composition. There was no partial lack of pattern and damage in the resulting black matrix. Observation of a section of the pattern using a scanning electron microscope confirmed no under-cut. Further, the observation of the black matrix using an optical microscope confirmed that there was no insoluble material on the area where no pattern was formed.

Example 7

A radiation sensitive composition was prepared by blending 120 parts by weight of a mixture of a red pigment (C.I. Pigment Red 177), an yellow pigment (C.I. Pigment Yellow 83), a green pigment (C.I. Pigment Green 7), and a blue pigment (C.I. Pigment Blue 15:6), at a ratio by weight of 10/2/2/5), as the component (A), 50 parts by weight of a copolymer of methacrylic acid/benzyl methacrylate/polystyrene macro monomer (copolymerization weight ratio: 25/65/10, weight average molecular weight: 55,000) as the component (B), 40 parts by weight of dipentaerythritol pentacrylate as the component (C), 10 parts by weight of 2,2'-bis(2-dibromophenyl)-4,4',5,5'-tetraphenylbiimidazole, 10 parts by weight of 4,4'-bis(diethylamino)benzophenone, and 20 parts by weight of 1-hydroxycyclohexylphenyl ketone, as the component (D), and 800 parts by weight of ethylene glycol monoethyl ether acetate as the component (E).

A black matrix in which a black pattern is formed on a substrate was produced in the same manner as in the Example 2 except using this radiation sensitive composition. There was no partial lack of pattern and damage in the resulting black matrix. Observation of a section of the pattern using a scanning electron microscope confirmed no under-cut. Further, the observation of the black matrix using an optical microscope confirmed that there was no insoluble material on the area where no pattern was formed.

Example 8

A radiation sensitive composition was prepared by blending 120 parts by weight of carbon black as the component (A), 50 parts by weight of a copolymer of methacrylic acid/benzyl methacrylate/polystyrene macro monomer (copolymerization weight ratio: 25/65/10, weight average molecular weight: 55,000) as the component (B), 40 parts by weight of dipentaerythritol pentacrylate as the component (C), 10 parts by weight of 2,2'-bis(2,4,6-trichlorophenyl)-4,4',5,5'-tetraphenylbiimidazole, 10 parts by weight of 4,4'-bis(diethylamino)benzophenone, and 5 parts by weight of 1-hydroxycyclohexylphenyl ketone, as the component (D), and 800 parts by weight of ethylene glycol monoethyl ether acetate as the component (E).

A black matrix in which a black pattern is formed on a substrate was produced in the same manner as in the Example 2 except using this radiation sensitive composition. There was no partial lack of pattern and damage in the resulting black matrix. Observation of a section of the pattern using a scanning electron microscope confirmed no under-cut. Further, the observation of the black matrix using an optical microscope confirmed that there was no insoluble material on the area where no pattern was formed.

Example 9

A radiation sensitive composition was prepared by blending 120 parts by weight of carbon black as the component (A), 50 parts by weight of a copolymer of methacrylic acid/benzyl methacrylate/2-hydroxyethyl methacrylate/polymethyl methacrylate macro monomer (copolymerization weight ratio: 15/60/15/10, weight average molecular weight: 55,000) as the component (B), 40 parts by weight of dipentaerythritol pentacrylate as the component (C), 10 parts by weight of 2,2'-bis(2-chlorophenyl)-4,4',5,5'-tetrakis(4-ethoxycarbonylphenyl)biimidazole, 5 parts by weight of 4,4'-bis(dimethylamino)benzophenone, 20 parts by weight of 1-hydroxycyclohexylphenyl ketone, and 2 parts by weight of 2-mercaptobenzothiazole as the component (D), and 800 parts by weight of ethylene glycol monoethyl ether acetate as the component (E).

A black matrix in which a black pattern is formed on a substrate was produced in the same manner as in the Example 2 except using this radiation sensitive composition. There was no partial lack of pattern and damage in the resulting black matrix. Observation of a section of the pattern using a scanning electron microscope confirmed no under-cut. Further, the observation of the black matrix using an optical microscope confirmed that there was no insoluble material on the area where no pattern was formed.

Because the radiation sensitive composition for color filters of the present invention contains biimidazole compound (1) and/or biimidazole compound (2) as essential components of the photopolymerization initiator, the composition exhibits excellent photographic sensitivity, superb contrast, and superior adhesion to substrates without producing any foreign material or insoluble material. The composition of the present invention can thus efficiently manufacture color filters with sharp pattern edges and with no lack or loss of pattern, and no under-cut.

Obviously, numerous modifications and variations of the present invention are possible in light of the above teachings. It is therefore to be understood that, within the scope of the appended claims, the invention may be practiced otherwise than as specifically described herein.

We claim:

1. A radiation sensitive composition for color filters comprising:

(A) a colorant consisting essentially of a pigment, (B) a binder polymer, (C) a poly-functional monomer, (D) a photopolymerization initiator which is at least one biimidazole compound selected from the group consisting of the compounds represented by the following general formula (1),

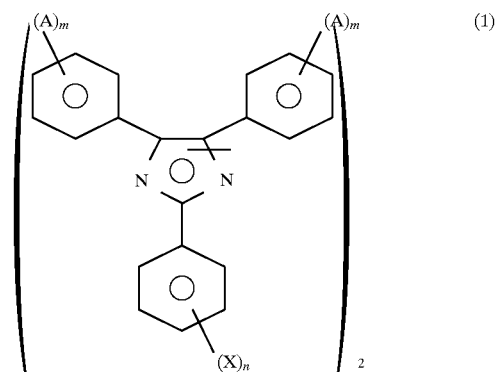

wherein X is a hydrogen atom, a halogen atom, a cyano group, an alkyl group having 1 to 4 carbon atoms, or an aryl group having 6 to 9 carbon atoms, A is a —COO—R group (wherein R is an alkyl group having 1 to 4 carbon atoms or an aryl group having 6 to 9 carbon atoms) m is an integer from 1 to 3, and n is an integer from 1 to 3, or the compounds represented by the following general formula (2),

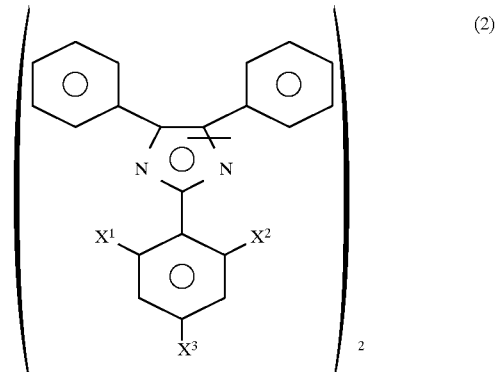

wherein $X^1$, $X^2$, and $X^3$ may be the same or different and each independently represents a hydrogen atom, a halogen atom, a cyano group, an alkyl group having 1 to 4 carbon atoms, or an aryl group having 6 to 9 carbon atoms, provided that two or more of $X^1$, $X^2$, and $X^3$ may not be a hydrogen atom at the same time, and (E) a solvent.

2. The radiation sensitive composition for color filters according to claim 1, wherein the component (B) is a carboxyl group-containing copolymer and the component (D) is at least one biimidazole compound of the general formula (1) selected from the group consisting of 2,2'-bis(2-chlorophenyl)-4,4',5,5'-tetrakis(4-ethoxycarbonylphenyl)biimidazole and 2,2'-bis(2-bromophenyl)-4,4',5,5'-tetrakis(4-ethoxycarbonylphenyl)biimidazole.

3. The radiation sensitive composition for color filters according to claim 1, wherein the component (B) is a carboxyl group-containing copolymer and the component (D) is at least one biimidazole compound of the general formula (2) selected from the group consisting of 2,2'-bis(2,4-dichlorophenyl)-4,4',5,5'-tetraphenylbiimidazole, 2,2'-bis(2,4-dibromphenyl)-4,4',5,5'-tetraphenylbiimidazole, 2,2'-bis(2,4,6-trichlorophenyl)-4,4',5,5'-tetraphenyl-biimidazole, and 2,2'-bis(2,4,6-tribromophenyl)-4,4',5,5'-tetraphenyl-biimidazole.

4. The radiation sensitive composition for color filters according to claim 2 or claim 3, wherein the component (D) further comprises one or more components selected from the group consisting of photo-radical generators other than the biimidazole compound of the general formula (1) or the biimidazole compound of the general formula (2), photosensitizers, curing promoters, and high polymer photo-cross-linking-agent or photosensitizers.

5. The radiation sensitive composition for color filters according to claim 2 or claim 3, wherein the carboxyl group-containing copolymer is at least one copolymer selected from the group consisting of methacrylic acid/benzyl methacrylate copolymer, methacrylic acid/benzyl methacrylate/styrene copolymer, methacrylic acid/methyl methacrylate/styrene copolymer, methacrylic acid/benzyl methacrylate/polystyrene macro monomer copolymer, methacrylic acid/benzyl methacrylate/polymethyl methacrylate macro monomer copolymer, methacrylic acid/methyl methacrylate/polystyrene macro monomer copolymer, methacrylic acid/methyl methacrylate/polymethyl methacrylate macro monomer copolymer, methacrylic acid/2-hydroxyethyl methacrylate/benzyl methacrylate/polystyrene macro monomer copolymer, and methacrylic acid/2-hydroxyethyl methacrylate/benzyl methacrylate/polymethyl methacrylate macro monomer copolymer.

6. The radiation sensitive composition for color filters according to claim 5, further comprising (F) an organic acid.

7. The radiation sensitive composition for color filters according to claim 1, wherein the component (C) is at least one compound selected from the group consisting of trimethylolpropane triacrylate, dipentaerythritol pentacrylate, and dipentaerythritol hexacrylate.

8. The radiation sensitive composition for color filters according to claim 1, wherein the component (A) is an organic pigment or carbon black.

9. The radiation sensitive composition for color filters according to claim 1, wherein component (D) is of formula (1).

10. The radiation sensitive composition for color filters according to claim 1, wherein component (D) is of formula (2).

11. The radiation sensitive composition for color filters according to claim 1, wherein colorant (A) consists of a pigment.

* * * * *

UNITED STATES PATENT AND TRADEMARK OFFICE
CERTIFICATE OF CORRECTION

PATENT NO. : 5,866,298
DATED : February 2, 1999
INVENTOR(S) : Satoshi IWAMOTO, et al.

It is certified that error appears in the above-indentified patent and that said Letters Patent is hereby corrected as shown below:

On the title page, Item [73], the Assignee information, should read:

--[73] Assignee: JSR Corporation, Tokyo, Japan--

Signed and Sealed this

Twelfth Day of October, 1999

*Attest:*

Q. TODD DICKINSON

*Attesting Officer*  Acting Commissioner of Patents and Trademarks